(12) United States Patent
Wick et al.

(10) Patent No.: US 10,941,059 B2
(45) Date of Patent: Mar. 9, 2021

(54) WATER DISINFECTION BODY FOR USE IN A WATER RESERVOIR

(71) Applicant: MIMBLY AB, Gothenburg (SE)

(72) Inventors: Michael Reidtz Wick, Solrød Strand (DK); Poul Fogh, Albertslund (DK); Stine Skotte Bjerregaard, Tikøb (DK)

(73) Assignee: MIMBLY AB, Gothenburg (SE)

( * ) Notice: Subject to any disclaimer, the term of this patent is extended or adjusted under 35 U.S.C. 154(b) by 0 days.

(21) Appl. No.: 16/199,282

(22) Filed: Nov. 26, 2018

(65) Prior Publication Data

US 2019/0092659 A1    Mar. 28, 2019

Related U.S. Application Data

(63) Continuation of application No. PCT/EP2017/062375, filed on May 23, 2017.

(30) Foreign Application Priority Data

May 24, 2016    (EP) .................................... 16171036

(51) Int. Cl.
*C02F 1/46* (2006.01)
*C02F 1/467* (2006.01)
(Continued)

(52) U.S. Cl.
CPC ........ *C02F 1/4674* (2013.01); *A47L 15/4238* (2013.01); *C02F 1/001* (2013.01);
(Continued)

(58) Field of Classification Search
CPC .. C02F 1/467; C02F 1/00; C02F 1/461; C02F 1/4674; C02F 1/46109; C02F 1/001;
(Continued)

(56) References Cited

U.S. PATENT DOCUMENTS 8,603,331 B1    12/2013  Koble
2009/0166280 A1*  7/2009  Dong ........................ C02F 3/06
210/202
(Continued)

FOREIGN PATENT DOCUMENTS

CN    201929921 U    8/2011
CN    104840164 A    8/2015
(Continued)

OTHER PUBLICATIONS

WO-2015154710-A1 Oct. 2015 Xiao Zhibang Translation full disclosure. (Year: 2015).*

*Primary Examiner* — Cameron J Allen
(74) *Attorney, Agent, or Firm* — Karceski IP Law, PLLC

(57) ABSTRACT

The present invention relates to an electrolysis body suitable for water disinfection for use in a water reservoir having a definite internal volume comprising a) a pair of electrodes made of a conductive material suitable for providing electrolysis, b) means for applying current to the electrodes, c) an insert unit having a first side and a second side opposite each other, wherein the first side faces out of the water reservoir when the insert unit is placed in position in the water reservoir in use for water disinfection and the second side faces into the volume of the water reservoir when placed in position in the water reservoir in use for water disinfection, and d) optionally a filter unit extending from the second side of the insert unit. The present invention also concerns a water reservoir comprising the body, as well as a washing system comprising the water reservoir.

14 Claims, 3 Drawing Sheets

(51) Int. Cl.
  *A47L 15/42* (2006.01)
  *C02F 1/00* (2006.01)
  *D06F 39/10* (2006.01)
  *D06F 35/00* (2006.01)
  *D06F 39/00* (2020.01)
  *C02F 1/461* (2006.01)
  *A47L 15/00* (2006.01)
  *C02F 1/42* (2006.01)
  *A61L 2/03* (2006.01)

(52) U.S. Cl.
  CPC ........ *C02F 1/46109* (2013.01); *D06F 35/003* (2013.01); *D06F 35/008* (2013.01); *D06F 39/006* (2013.01); *D06F 39/10* (2013.01); *A47L 15/0057* (2013.01); *A61L 2/035* (2013.01); *C02F 1/42* (2013.01); *C02F 2001/46133* (2013.01); *C02F 2001/46152* (2013.01); *C02F 2201/46115* (2013.01); *C02F 2303/04* (2013.01); *C02F 2307/12* (2013.01); *D06F 39/007* (2013.01)

(58) Field of Classification Search
  CPC ........ C02F 2307/12; C02F 2001/46152; C02F 2001/46133; C02F 2201/46115; C02F 2303/04; A47L 15/42; A47L 15/4238; D06F 35/00; D06F 39/10; D06F 35/008
  See application file for complete search history.

(56) References Cited

U.S. PATENT DOCUMENTS

| | | | |
|---|---|---|---|
| 2011/0198300 A1* | 8/2011 | Sadolin | C02F 1/4674 210/748.2 |
| 2014/0217035 A1 | 8/2014 | Poyet | |
| 2014/0326680 A1* | 11/2014 | Mastio | C25B 1/26 210/747.5 |
| 2017/0114489 A1* | 4/2017 | Spill | D06F 35/003 |

FOREIGN PATENT DOCUMENTS

| | | | | |
|---|---|---|---|---|
| EP | 2397062 A2 | 12/2011 | | |
| JP | 2003093311 A | 4/2003 | | |
| WO | WO-2015154710 A1 * | 10/2015 | ............. | C02F 1/461 |
| WO | 2016182548 A1 | 11/2016 | | |

* cited by examiner

US 10,941,059 B2

WATER DISINFECTION BODY FOR USE IN A WATER RESERVOIR

This application is the continuation of International Application No. PCT/EP2017/062375, filed 23 May 2017, which claims the benefit of European Patent Application No. EP 16171036.3, filed 24 May 2016, the entire contents of which are hereby incorporated by reference.

FIELD OF THE INVENTION

The present invention relates to an electrolysis body suitable for water disinfection for use in a water reservoir. The invention also concerns a water reservoir comprising the electrolysis body. Moreover, water systems, such as a dish washer equipped with a water reservoir for storing washing liquid comprises the electrolysis body of the present invention.

BACKGROUND OF THE INVENTION

Dishwashers are used in domestic kitchens as well as professional kitchens and restaurants for dishing goods such as for example plates, pots, pans etc. Dishwashers comprises a washing chamber in which the dishing goods are packed in one or more baskets to remain in the intended position separated from adjacent items to make it possible for water to circulate within the washing chamber and clean the cups, plates, cutlery etc. Water is circulated in the washing chamber by a pump arranged in the lower section of the washing chamber. The water is lead from the pump via pipes to one, or more, rotating spray arms provided with a number of nozzles that are spraying water on the dishing goods to clean the dishing goods.

In US20150047679 a dishwasher comprising a washing chamber in which dishes to be cleaned are placed. Washing liquid is sprayed into the washing chamber by means of a circulation pump for cleaning and/or rinsing the dishes. Washing liquid may be circulated in the dishwasher in different washing cycles. Thus, a dishwashing operation may comprise for instance, a prewashing cycle during which the dishes are cleaned with water only, a main washing cycle during which the dishes are cleaned with water and detergent, and a rinsing cycle during which the dishes are rinsed with water and a rinsing agent. Water admitted into the dishwasher may be softened, e.g. by means of an ion exchange resin. In WO 2009/027320 is disclosed a domestic dishwasher comprising a treatment chamber, in which items to be washed are supplied with washing liquid, and a reservoir that functions as a heat exchanger. The reservoir is in thermal contact with an outer wall of the dishwasher and in thermal contact with the treatment chamber. The reservoir is filled with fresh water by means of supply means. The water in the reservoir is pre-heated inter alia by means of heated washing liquid in the treatment chamber. The contents of the reservoir can be introduced via outlet lines into the treatment chamber. The dishwasher is equipped with recycling means that deliver washing liquid from the treatment chamber to the reservoir. The water reservoir for containing water for, for instance, re-circulation is an integrated part of the dish washer, wherein the water in the reservoir may stand for hours, days or weeks without being used and create microbial growth.

The problem of microbial growth in such water reservoirs is has been solved as described hereinafter.

SUMMARY OF THE INVENTION

The present invention concerns an electrolysis body suitable for water disinfection for use in a water reservoir. This body provides for the first time a means for disinfection of water in a water reservoir containing water for re-circulation, wherein the water in the reservoir may stand for hours, days or weeks without being used and create microbial growth, making the water unsuitable for use unless disinfected. The water reservoir is typically an integrated part of a washing system, such as a dish washer or washing machine, and has an internal volume of 1 to 10 liters making it suitable for integration in a dish washer or washing machine. When for instance the washing system is a dishwasher, washing liquid, e.g. tap water, is sprayed into a washing chamber for cleaning dishes and is being circulated in different washing cycles. In this respect, a water reservoir for maintaining and recirculating cleaning water is typically integrated in the dishwasher to save water, however, microbial growth is a serious health problem that the present inventors have solved. Where the classical means of keeping the microbiology under control involves replacing the water after use or increasing temperature during storage—at least periodically—to above 65° C., both these methods have severe drawbacks as they either use a lot of water, or cost a lot of energy and increase the wear and tear and corrosion of the machine. Alternatively, one can add chemistry, but this involves chemicals and frequent user action (both unwanted from a consumer view).

Electrochlorination is in this respect much gentler and offers the possibility of maintaining control of the microbiology without any user action or handling of chemicals. The power consumption is much lower than thermal treatment as well.

In a broad aspect the present invention relates to an electrolysis body suitable for water disinfection for use in a water reservoir having a definite internal volume comprising a) a pair of electrodes made of a conductive material suitable for providing electrolysis, b) means for applying current to the electrodes, c) an insert unit having a first side and a second side opposite each other, wherein the first side faces out of the water reservoir when the insert unit is placed in position in the water reservoir in use for water disinfection and the second side faces into the volume of the water reservoir when placed in position in the water reservoir in use for water disinfection, and d) optionally a filter unit extending from the second side of the insert unit, wherein (i) the pair of electrodes is arranged and fixed in the insert unit and protrude from the second side,
(ii) optionally the pair of electrodes is surrounded or partly surrounded by the filter unit,
(iii) the means for applying current to the pair of electrodes is arranged and fixed in the insert unit and protrude from the first side, and
(iv) the insert unit is adapted for being arranged in an opening in the water reservoir and for a water tight sealing of the water reservoir when in use for water disinfection.

In an embodiment the pair of electrodes is parallel and symmetrically arranged electrode plates made of a conductive material and having a suitable distance for providing electrolysis, wherein the pair of electrode plates are arranged and fixed in the insert unit and protrude from the second side, and having means for applying current to the electrode plates. In a further embodiment the pair of parallel and symmetrically arranged electrode plates have a distance selected from 0.5-10 mm, such as 1-8 mm, typically 1-5 mm. In a further embodiment the electrolysis body has one pair of parallel and symmetrically arranged perforated electrode plates. In a further embodiment the pair of electrodes are perforated electrodes, such as perforated electrode plates. In a still further embodiment the pair of electrodes, such as electrode plates, are made of expanded metal.

In a further embodiment the pair of electrodes extends perpendicular from the second side of the insert unit. Typically, the electrodes extend from 10 to 50 mm, such as from 15 to 30 mm, e.g. about 25 mm.

In a still further embodiment the filter unit is present and the pair of electrodes is surrounded or partly surrounded by the filter unit. In an embodiment the filter unit surrounds the electrode or electrode plates. In another embodiment the filter unit partly surrounds the electrode or electrode plates.

Alternatively, the filter unit is not present and the pair of electrodes not surrounded by any filter unit. In this respect, it is preferred to adapt a filter unit at the inlet opening of the water reservoir for supplying water to the reservoir. This embodiment is explained below in connection with description of the water reservoir of the present invention.

In a still further embodiment the insert unit and filter unit are integrated into one unit.

In a further embodiment the filter is circular. Typically, the filter has a diameter from 40 to 150 mm. Such as from 60 to 100, e.g. from 75 to 90 mm, typically from 75-85 mm.

In a still further embodiment the insert unit is circular. Typically, the insert unit has a diameter from 40 to 150 mm. Such as from 60 to 100, e.g. from 75 to 90 mm, typically from 80-90 mm.

In a further embodiment both the insert unit and filter unit are circular.

In a still further embodiment the filter unit extends perpendicular from the insert unit. Typically, the filter extends from 10 to 50 mm, such as from 15 to 30 mm, e.g. about 20 mm.

In a further embodiment the filter is selected from a membrane and a polymer made of a material that does not degrade in the presence of an oxidizing disinfectant, such as chlorine.

In a still further embodiment the filter unit comprises circular through holes.

In a further embodiment the filter unit is made from the same material as the insert unit. Typically, any polymer non-conductive and/or any non-corrosive material that will withstand chlorine is suitable. Preferably the filter unit and insert unit are made from poly ethylene (PE), polypropylene (PP) or akrylonitril-butadien-styren (ABS).

In a further embodiment the filter is selected from the polymer made of a material selected from a fluorinated hydrocarbon polymer and a polyether-sulfonic polymer.

In a still further embodiment the filter comprises a ceramic material selected from any one of Diatomite, Silicon Carbide, Alumina Oxide, Titanium Oxide, Zirconium Oxide, stabilized Zirconium Oxide, or mixtures thereof, or mixtures where the major component thereof is one of Silicon Carbide, Alumina Oxide, Titanium Oxide, Zirconium Oxide, or stabilized Zirconium Oxide.

In a further aspect the present invention relates to a water reservoir having an inlet opening for supplying water to the reservoir and an outlet opening for letting water out of the reservoir adapted to be connected to water mains, comprising an electrolysis body suitable for water disinfection for use in a water reservoir having a definite internal volume comprising a) a pair of electrodes made of a conductive material suitable for providing electrolysis, b) means for applying current to the electrodes, c) an insert unit having a first side and a second side opposite each other, wherein the first side faces out of the water reservoir when the insert unit is placed in position in the water reservoir in use for water disinfection and the second side faces into the volume of the water reservoir when placed in position in the water reservoir in use for water disinfection, and d) optionally a filter unit extending from the second side of the insert unit, wherein (i) the pair of electrodes is arranged and fixed in the insert unit and protrude from the second side,
(ii) optionally the pair of electrodes is surrounded or partly surrounded by the filter unit,
(iii) the means for applying current to the pair of electrodes is arranged and fixed in the insert unit and protrude from the first side, and
(iv) the insert unit is adapted for being arranged in an opening in the water reservoir and for a water tight sealing of the water reservoir when in use for water disinfection.

In a still further aspect the present invention relates to a water reservoir having an inlet opening for supplying water to the reservoir and an outlet opening for letting water out of the reservoir adapted to be connected to water mains, comprising any one of the above embodiments for the electrolysis body of the present invention.

In an embodiment the internal volume is from 1 to 10 liters, such as from 2-8 liters, e.g. 3-6 liters, such as about 4 liters.

In another embodiment the reservoir is a grey water tank, such as a grey water tank having an internal volume of at least 50 liters, e.g. from 50 liters to 10 m$^3$.

In a further embodiment the water reservoir has at least two electrolysis bodies selected from any one of the above embodiments for the electrolysis body of the present invention, such as from 2 to 10 electrolysis bodies, e.g. 4-8 electrolysis bodies, typically 6 electrolysis bodies.

In a further embodiment the bodies are adapted for electricity connected in series.

In a further embodiment the bodies are adapted for electricity connected in parallel.

Alternatively, there is no filter unit surrounding or partly surrounding the pair of electrodes. In an embodiment a filter unit is adapted at the inlet opening of the water reservoir for supplying water to the reservoir. It is to be understood that both a filter unit at the inlet opening and a filter unit surrounding or partly surrounding the pair of electrodes may be present at the same time.

In a still further aspect the present invention relates to a washing system comprising a water reservoir for maintaining and recirculation of water for cleaning wherein the water reservoir has an inlet opening for supplying water to the reservoir and an outlet opening for letting water out of the reservoir adapted to be connected to water mains, comprising an electrolysis body suitable for water disinfection for use in a water reservoir having a definite internal volume comprising a) a pair of electrodes made of a conductive material suitable for providing electrolysis, b) means for applying current to the electrodes, c) an insert unit having a first side and a second side opposite each other, wherein the first side faces out of the water reservoir when the insert unit is placed in position in the water reservoir in use for water disinfection and the second side faces into the volume of the water reservoir when placed in position in the water reservoir in use for water disinfection, and d) optionally a filter unit extending from the second side of the insert unit, wherein (i) the pair of electrodes is arranged and fixed in the insert unit and protrude from the second side,
(ii) optionally the pair of electrodes is surrounded or partly surrounded by the filter unit, (iii) the means for applying current to the pair of electrodes is arranged and fixed in the insert unit and protrude from the first side, and the insert unit is adapted for being arranged in an opening in the water reservoir and for a water tight sealing of the water reservoir when in use for water disinfection.

In a still further aspect the present invention relates to a washing system comprising a water reservoir for maintaining and recirculation of water for cleaning wherein the water reservoir is selected from any one of the above embodiments for the water reservoir of the present invention.

In an embodiment the washing system is selected from a dish washer and a washing machine. In one embodiment the washing system is selected from a dish washer. A typical dish washer is described in US20150047679.

In a further embodiment the water reservoir is an integrated part of the washing system, such as the dish washer or the washing machine.

In a further aspect the present invention relates to use of an electrolysis body suitable for water disinfection for use in a water reservoir having a definite internal volume comprising a) a pair of electrodes made of a conductive material suitable for providing electrolysis, b) means for applying current to the electrodes, c) an insert unit having a first side and a second side opposite each other, wherein the first side faces out of the water reservoir when the insert unit is placed in position in the water reservoir in use for water disinfection and the second side faces into the volume of the water reservoir when placed in position in the water reservoir in use for water disinfection, and d) optionally a filter unit extending from the second side of the insert unit, wherein (i) the pair of electrodes is arranged and fixed in the insert unit and protrude from the second side,
(ii) optionally the pair of electrodes is surrounded or partly surrounded by the filter unit,
(iii) the means for applying current to the pair of electrodes is arranged and fixed in the insert unit and protrude from the first side, and
(iv) the insert unit is adapted for being arranged in an opening in the water reservoir and for a water tight sealing of the water reservoir when in use for water disinfection;

for disinfection of water in a water reservoir, wherein the water is for cleaning in a washing system. In an embodiment the washing system is a dish washer. In a further embodiment current is applied to the means for applying current to the electrode and reversed in a time interval of from 10 minutes to 60 minutes, typically every 30 minutes.

The present invention provides all of these advantages with the described solution.

Further objects and advantages of the present invention will appear from the following description, and claims.

SHORT DESCRIPTION OF DRAWINGS

DESCRIPTION OF THE INVENTION

Figure 1:
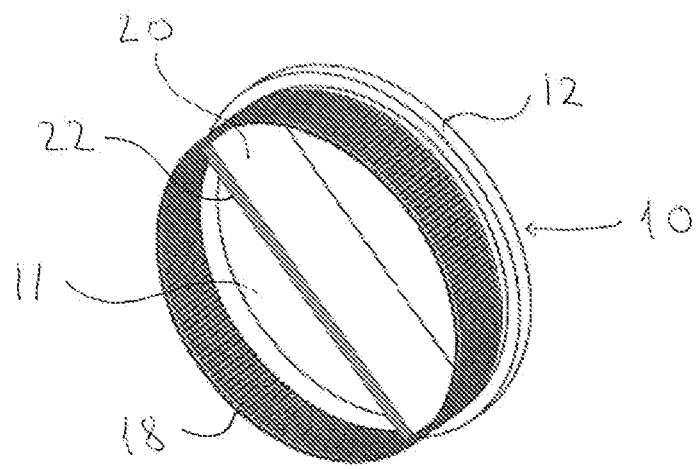
FIG. 1 illustrates an electrolysis body of the present invention seen in a 3D perspective-like view showing the body from an angle that faces into a water reservoir, such as a plastic container suitable for a dishwasher machine.

The present invention concerns an electrolysis body (10) suitable for water disinfection for use in a water reservoir (50) having a definite internal volume (52) comprising a) a pair of electrodes (20, 22) made of a conductive material suitable for providing electrolysis, b) means (14, 16) for applying current to the electrodes, c) an insert unit (12) having a first side (24) and a second side (26) opposite each other, wherein the first side faces out of the water reservoir when the insert unit is placed in position in the water reservoir (50) in use for water disinfection and the second side faces into the volume (52) of the water reservoir when placed in position in the water reservoir in use for water disinfection, and d) optionally a filter unit (18) extending from the second side of the insert unit, wherein (i) the pair of electrodes is arranged and fixed in the insert unit and protrude from the second side,
(ii) optionally the pair of electrodes is surrounded or partly surrounded by the filter unit,
(iii) the means for applying current to the pair of electrodes is arranged and fixed in the insert unit and protrude from the first side, and
(iv) the insert unit is adapted for being arranged in an opening in the water reservoir and for a water tight sealing of the water reservoir when in use for water disinfection.

In another aspect the present invention concerns an electrolysis body (10) suitable for water disinfection for use in a water reservoir (50) having a definite internal volume (52) comprising a) a pair of electrodes (20, 22) made of a conductive material suitable for providing electrolysis, b) means (14, 16) for applying current to the electrodes, c) an insert unit (12) having a first side (24) and a second side (26) opposite each other, wherein the first side faces out of the water reservoir when the insert unit is placed in position in the water reservoir (50) in use for water disinfection and the second side faces into the volume (52) of the water reservoir when placed in position in the water reservoir in use for water disinfection, wherein (i) the pair of electrodes is arranged and fixed in the insert unit and protrude from the second side,
(ii) the means for applying current to the pair of electrodes is arranged and fixed in the insert unit and protrude from the first side, and
(iii) the insert unit is adapted for being arranged in an opening in the water reservoir and for a water tight sealing of the water reservoir when in use for water disinfection.

In a further aspect the present invention concerns an electrolysis body (10) suitable for water disinfection for use in a water reservoir (50) having a definite internal volume (52) comprising a) a pair of electrodes (20, 22) made of a conductive material suitable for providing electrolysis, b) means (14, 16) for applying current to the electrodes, c) an insert unit (12) having a first side (24) and a second side (26) opposite each other, wherein the first side faces out of the water reservoir when the insert unit is placed in position in the water reservoir (50) in use for water disinfection and the second side faces into the volume (52) of the water reservoir when placed in position in the water reservoir in use for water disinfection, and d) a filter unit (18) extending from the second side of the insert unit, wherein
  (i) the pair of electrodes is arranged and fixed in the insert unit and protrude from the second side,
  (ii) the pair of electrodes is surrounded or partly surrounded by the filter unit,
  (iii) the means for applying current to the pair of electrodes is arranged and fixed in the insert unit and protrude from the first side, and
  (iv) the insert unit is adapted for being arranged in an opening in the water reservoir and for a water tight sealing of the water reservoir when in use for water disinfection.

The term "a water reservoir" as used herein means a housing, such as a container or tank made of any suitable material, such as metal or plastics, that is adapted for containing water to be disinfected. The water reservoir has a definite internal volume meaning that the internal volume is constant during use in the washing system, such a dish washer. In respect of a dish washer or a washing machine the definite internal volume is typically up to ten liters. In respect of a grey water tank, the definite internal volume is typically of at least 50 liters, such as up to 10 $m^3$.

The term "a pair of electrodes made of a conductive material" as used herein means one or more pairs of electrodes, such as one or more pairs of electrode plates. Preferably the electrode is a pair of parallel and symmetrically arranged electrode plates (20, 22), such as perforated electrode plates, made of a conductive material, such as expanded metal, and having a suitable distance for providing electrolysis. An example of such an electrode is disclosed in PCT/DK2009/000215. The conductive material is without limitation selected from a metal such as copper, aluminium, titanium, doped diamond, tin, silver, nickel, platinum, iron, lead, and oxides thereof, and alloys thereof. Typically, the electrode plates are made of titanium covered with ruthenium/iriduim oxide.

The term "means for applying current to the pair of electrodes" as used herein defines an element which protrudes from the insert unit on one side of the insert unit, which can be connected to a current supply, and which is in electrical communication with the pair of electrodes, such as electrode plates, which protrudes from the opposite side of the insert unit. The means for applying current to the electrode is fixed in the insert unit in a fluid tight, such as water tight, manner so that water in the water reservoir cannot escape the reservoir.

The term "an insert unit" as used herein means a unit which is used to close the openings in the water reservoir to create a fluid tight, such as water tight, sealing of the water reservoir. The insert unit, may be seen as a plug equipped with a thread, glue, bracket or snapping or other means known to the skilled person to secure tight closure.

The term "a filter unit" as used herein when present as part of the electrolysis body comprises a filter which extends from the second side of the insert unit, in the same direction as the pair of electrode or electrode plates. The filter is without limitation made of a material that does not degrade in the presence of an oxidizing disinfectant. Typically, the oxidizing disinfectant is selected from chlorine, ozone, peroxides, and/or free radicals. The filter material may be selected from a polymer material such as a fluorinated hydrocarbon polymer or a polyether sulfonic polymer, e.g. PolyEtherSulfonate (PES) and Flourinated membrane (PTFE/PVDF etc.) and other types of polymer. The filter may also be selected from a ceramic material, such as a type of solid crystaline materials, typically metal salts, which offer good resistance to oxidizing agents and are without limitation selected from Diatomite, Silicon Carbide, Alumina Oxide, Zirconium Oxide, stabilized Zirconium Oxide, or mixtures thereof. The filter may be a simple polymer material comprising through holes which holes may be circular or rectangular. When, as an alternative, a filter unit is adapted at the inlet opening of the water reservoir such filter unit may be selected from the above same materials.

When the filter unit is present as part of the electrolysis body, the pair of electrode plates is arranged and fixed in the insert unit and protrude from the second side of the insert unit in the same direction as the filter unit. The electrodes may be surrounded or partly surrounded by the filter unit. When the filter unit surrounds the electrode it means that a defined space is created by the filter unit and the insert unit in which space the electrodes is placed. When the filter unit partly surrounds the electrodes it means that the filter unit has one or more openings of a size that does not perform a filtering effect. For instance, when the filter unit is circular and extends perpendicular from the second side of the insert unit it partly surrounds the electrodes and leaves an opening facing opposite and away from the second side of the insert unit. In this instance, the pair of electrode plates also extends perpendicular from the second side of the insert unit.

In a typical embodiment the insert unit and filter unit are integrated into one unit. In another embodiment the insert unit and filter unit are two separate units that are assembled before use in the water reservoir.

Typically, the water to be disinfected comprises some amount of chlorine, in the form of chloride ions, and preferably the water to be disinfected contain at least 2 ppm, such as at least 5 ppm, such as at least 7 ppm, e.g. at least 10 ppm of chloride ions. Typically, the water to be disinfected contain from 10 ppm to 250 ppm of chloride ions. It is obvious to the skilled person, that the higher the chloride content, the more chlorine can be produced.

In a further embodiment the water to be disinfected contain at least 10 ppm of chloride ions and has an electrical conductivity of at least 100 μS/cm. Typically, the water has an electrical conductivity of from 200 μS/cm to 1000 μS/cm. The skilled person will know that it is possible if the chloride content is high to operate at lower conductivities. It is obvious to the skilled person, that the higher the conductivity, the lower voltage to run the electrolysis process.

The water entering the water reservoir may be treated to soften the water before entering the reservoir. This has the advantage that the forced precipitation of hardness on the electrodes is prevented and thus ensuring uninterrupted disinfection. Thus, in a further embodiment the water has been softened before entering the water inlet. Preferably the water has been softened to a hardness level, which measured by the dH scale should be below 5. Typically, the water has been softened by an ion exchanger. Thus, in a further embodiment of the washing system a water softener, such as an ion exchanger, is placed before water inters the water reservoir via the inlet opening.

The present inventors have provided a new device for killing bacteria described in PCT/DK2009/000215, containing a pair of parallel and symmetrically arranged perforated electrode plates, which electrodes are also suitable for use in the present invention. Thus, in a further embodiment the electrode comprises a pair of parallel and symmetrically arranged perforated electrode plates having a suitable distance, wherein each pair is optionally fitted with a fuse, wherein a suitable current density is applied, and wherein the plates are made of a conductive material and are arranged in a perpendicular plane. Typically, the pair of parallel and symmetrically arranged perforated electrode plates has/have a distance selected from 1-5 mm, such as 1, 2, 3, 4 or 5 mm and combinations thereof. The electrodes are arranged in pairs that may have the same distance between the plates or may have different distance between the plates, if more than one pair of electrodes is present. Typically, from 1 to 11 pairs of parallel and symmetrically arranged perforated electrode plates are present, such as 1-10, 2-9, 3-8, 4-7, or 5-6 pairs of parallel and symmetrically arranged perforated electrode plates.

When a pair of parallel and symmetrically arranged electrode plates, such as perforated plates, is used, such pair of parallel and symmetrically arranged electrode plates is optionally arranged such that in a perpendicular plane view 60-100% of the area of passage is inserted by the electrodes.

Typically, the current density is above 5 mA/cm$^2$, such as from 5 to 30 mA/cm$^2$.

In a further embodiment the polarity of the electrodes can be reversed.

DRAWINGS

The invention will now be described more fully with reference to the appended drawings illustrating typical embodiments of the electrolysis body suitable for water disinfection for use in a water reservoir. These drawings are by no means limiting the scope of the present invention and are only intended to guide the skilled person for better understanding of the present invention.

FIG. 1 illustrates an electrolysis body (10) of the present invention seen in a 3D perspective-like view showing the body (10) from an angle that faces into a water reservoir (not shown), such as a plastic container suitable for a dishwasher machine. The body (10) consists of an insert unit (12) having a first side (indicated in FIG. 2 as (24)) and a second side (indicated in FIG. 2 as (26)) wherein the first and second sides are opposite each other. From the insert unit (12) which is shown as a circular unit, a filter unit (18) comprising a circular filter extending perpendicular from the second side of the insert unit is shown. Further shown is one pair of electrode plates (20, 22) extending perpendicular from the second side of the insert unit (12). The insert unit (12), the filter unit (18) and filter partly surrounds the electrode plates (20, 22) and leaves an opening (11) facing opposite and away from the second side of the insert unit (12).

Figure 2:
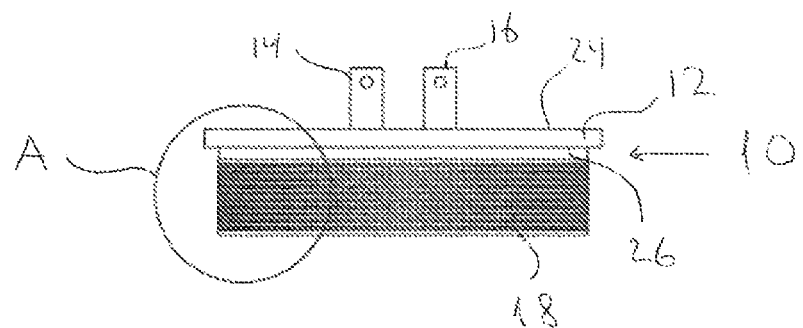
FIG. 2 illustrates the electrolysis body of the present invention seen from the side.

FIG. 2 illustrates the electrolysis body (10) of the present invention seen from one side, wherein the filter unit (18) comprising the filter extends perpendicular from the second side (26) of the insert unit (12). The means for applying current to the pair of electrodes (14, 16) can be seen protruding from the first side (24) of the insert unit (12). A certain section A (circled) is rotated and blown up in FIG. 3.

Figure 3:
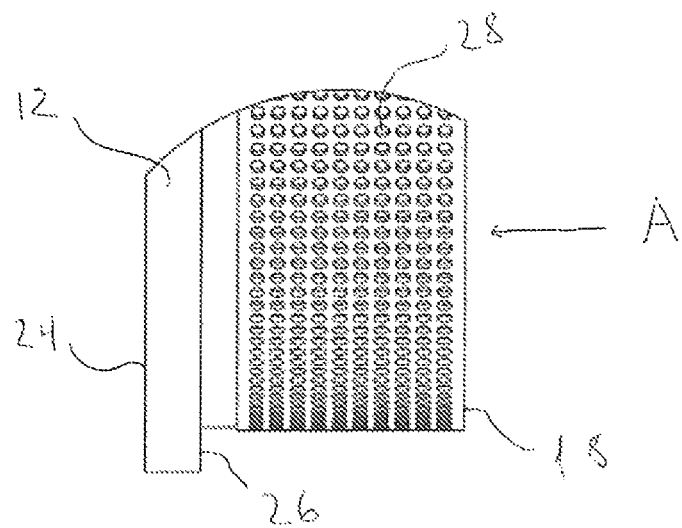
FIG. 3 illustrates a part of the electrolysis body of the present invention showing circular through holes in the filter unit, although such holes may also be rectangular or any other suitable shape as long as they perform the intended filtering effect.
Figure 7:
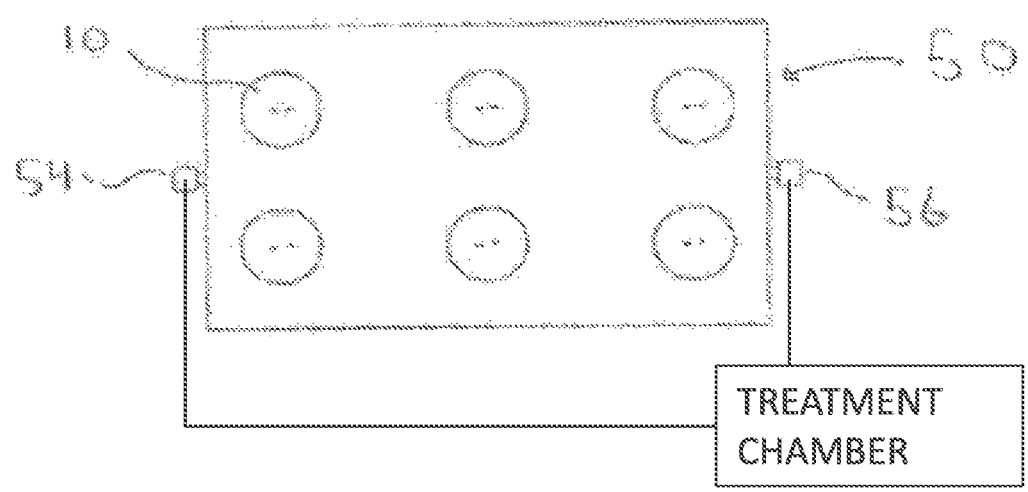
FIG. 7 illustrates a water reservoir seen from a side with 6 electrolysis bodies of the present invention and in- and outlets.
Figure 8:
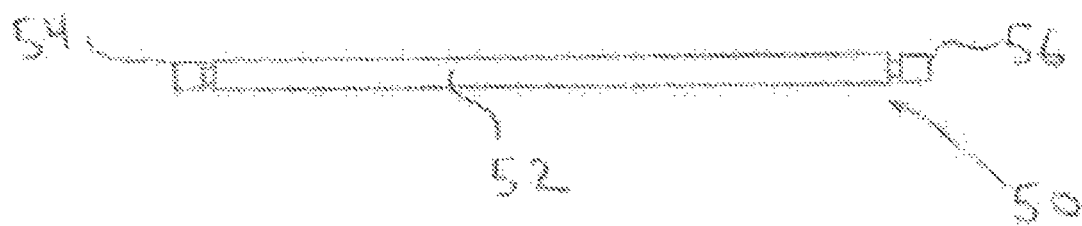
FIG. 8 illustrates the water reservoir seen from another side with in- and outlets.

FIG. 3 illustrates a part of the electrolysis body (10) of the present invention showing circular through holes (28) in the filter of the filter unit (18), although such holes may also be rectangular or any other suitable shape as long as they perform the intended filtering effect, when the body (10) is adapted for use in the water reservoir (shown in FIGS. 7 and 8 as (50)).

Figure 4:
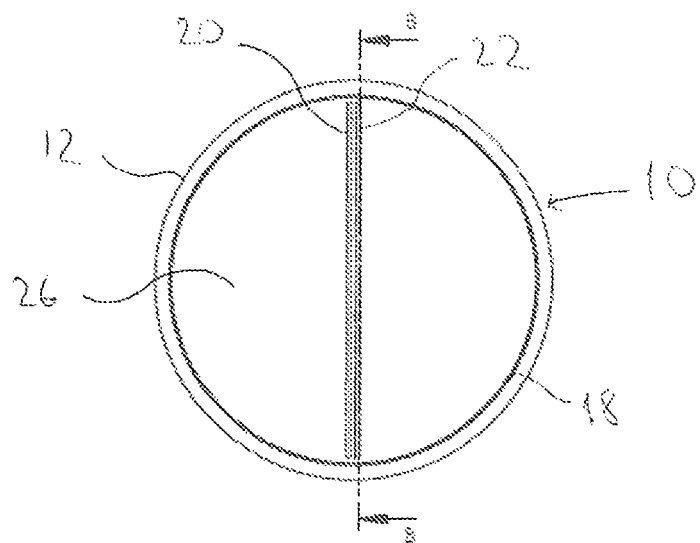
FIG. 4 illustrates the electrolysis body of the present invention seen from the side that faces into a water reservoir and showing a cross section B.

FIG. 4 illustrates the electrolysis body (10) of the present invention seen from the side that faces into a water reservoir and showing a cross section B. The section B is made through one of the electrode plates (22) and shown in FIG. 5 as indicated by the arrows in FIG. 4.

Figure 5:
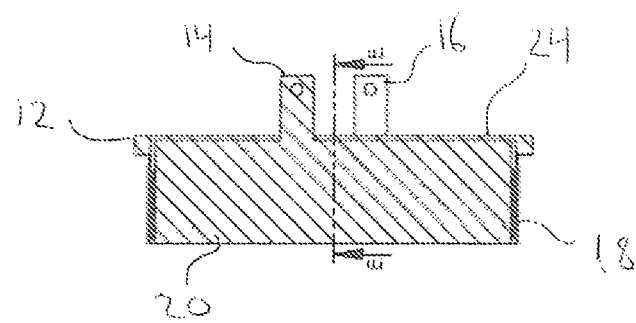
FIG. 5 illustrates the electrolysis body of the present invention along the cross sectional view B indicated in FIG. 4, and further showing a cross section E.

FIG. 5 illustrates the electrolysis body (10) of the present invention along the cross sectional view B indicated in FIG. 4. A further cross section E is indicated by arrows and shown in FIG. 6.

Figure 6:
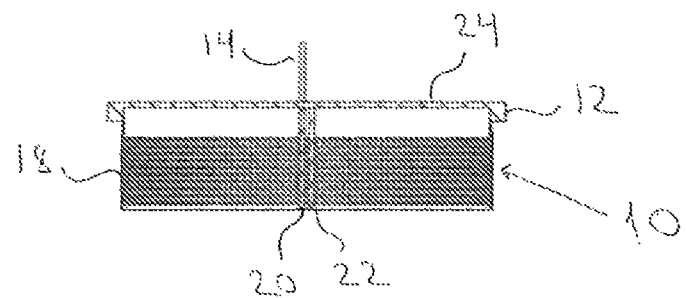
FIG. 6 illustrates the electrolysis body of the present invention along the cross sectional view E indicated in FIG. 5.

FIG. 6 illustrates the electrolysis body (10) of the present invention along the cross sectional view E indicated in FIG. 5.

FIG. 7 illustrates a water reservoir (50) seen from a side with 6 electrolysis bodies (10) of the present invention. The water reservoir (50) has an inlet opening (54) for supplying water to the reservoir (50) during use in a water system, such as a dish washer, and an outlet opening (56) for letting water out of the reservoir (50) during use in a water system, such as a dish washer.

FIG. 8 illustrates the water reservoir (50) with the inlet opening (54) and the outlet opening (56) seen from another side where the electrolysis bodies (10) are concealed. The bodies (10) are arranged in openings (as indicated in FIG. 7) and the filter and electrode plates extends into the internal volume (52).

All references, including publications, patent applications and patents, cited herein are hereby incorporated by reference to the same extent as if each reference was individually and specifically indicated to be incorporated by reference and was set forth in its entirety herein.

All headings and sub-headings are used herein for convenience only and should not be construed as limiting the invention in any way.

Any combination of the above-described elements in all possible variations thereof is encompassed by the invention unless otherwise indicated herein or otherwise clearly contradicted by context.

Recitation of ranges of values herein are merely intended to serve as a short method of referring individually to each separate value falling within the range, unless other-wise indicated herein, and each separate value is incorporated into the specification as if it were individually recited herein. Unless otherwise stated, all exact values provided herein are representative of corresponding approximate values (e.g., all exact exemplary values provided with respect to a particular factor or measurement can be considered to also provide a corresponding approximate measurement, modified by "about", where appropriate).

All methods described herein can be performed in any suitable order unless other-wise indicated herein or otherwise clearly contradicted by context.

The terms "a" and "an" and "the" and similar referents as used in the context of de-scribing the invention are to be construed to insert both the singular and the plural, unless otherwise indicated herein or clearly contradicted by context. Thus, "a" and "an" and "the" may mean at least one, or one or more.

The use of any and all examples, or exemplary language (e.g., "such as") provided herein, is intended merely to better illuminate the invention and does not pose a limitation on the scope of the invention unless otherwise indicated. No language in the specification should be construed as indicating any element is essential to the practice of the invention unless as much is explicitly stated.

The citation and incorporation of patent documents herein is done for convenience only and does not reflect any view of the validity, patentability and/or enforceability of such patent documents.

The description herein of any aspect or embodiment of the invention using terms such as "comprising", "having", "including" or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

This invention includes all modifications and equivalents of the subject matter re-cited in the aspects or claims presented herein to the maximum extent permitted by applicable law.

The features disclosed in the foregoing description may, both separately and in any combination thereof, be material for realizing the invention in diverse forms thereof.

Description of the Preferred Electrochemical Disinfection Method in a Dishwasher In one embodiment a dishwasher comprises a washing chamber with a sump and a circulation circuit, the circulation circuit comprising the sump, a circulation pump and a spraying device for spraying washing liquid into the washing chamber, the dishwasher further comprising a water reservoir adapted to be connected to water mains, wherein a liquid connection is adapted to transfer liquid from the reservoir to the washing chamber, and wherein a return system is adapted to transfer liquid from the washing chamber to the reservoir, wherein the reservoir is thermally insulated from the washing chamber. The water reservoir comprises from 4-8 electrolysis bodies, such as 6, wherein each body comprises a) one pair of electrodes made of titanium covered with ruthenium/iridium oxide suitable for providing electrolysis, b) means for applying current to the electrodes, c) an insert unit placed in position in the water reservoir, and d) a filter unit,
wherein
  (i) the pair of electrodes is arranged and fixed in the insert unit and protrude into the water reservoir,
  (ii) the pair of electrodes is surrounded by the filter unit,
  (iii) the means for applying current to the pair of electrodes is arranged and fixed in the insert unit, and
  (iv) the insert unit is threaded in an opening in the water reservoir and creates a water tight sealing of the water reservoir.

When operating the dishwasher, such operation comprises:
  circulating washing liquid in the circulation circuit,
  tapping freshwater from water mains into the reservoir, and
  heating the washing liquid circulating in the circulation circuit without a washing liquid temperature being affected by a water temperature of the freshwater in the reservoir.

Once the washing cycle has been completed, the final rinse water, is stored in the reservoir. Immediately after the completion, power is applied to the electrodes. Eg, six inserts could be arranged in parallel and be fed with a total current of 4-2-1-0.5 Amps, the voltage depending on the conductivity of the water. To the knowing expert, it is obvious, that a serial arrangement would require approximately 6 times the voltage, but only a sixth of the current to obtain the same chlorine production. The power is applied for 2-60 minutes, and the process is repeated at intervals, (from 30 minutes hour to 24 hours, such as 6 hours) to chlorinate the water. Once a new washing cycle is started, the water is used for initial washing, and the water in the tank is replaced. In any case, the washing machine may dump and replace the water after a period of time.

EXPERIMENTAL

Experiments show that in a water tank of 15 L, 3 minutes of electrolysis per day in a setup with a single set of electrodes supplied at 12 VDC and 1 A, kept the tank clean. This means that a similar setup running around the clock (24 hour cycles) can keep a 7 $m^3$ tank clean.

We claim:
1. A washing system selected from at least one of a dishwasher or washing machine, comprising:
  a treatment chamber for receiving items to be washed,
  a water reservoir, separate from the treatment chamber, for maintaining and recirculating water for cleaning to the treatment chamber, the water reservoir having an inlet opening for supplying water to the water reservoir, an outlet opening for letting water out of the water reservoir into the treatment chamber, and a definite internal volume,
  an electrolysis body disposed in the water reservoir comprising:
    a) a pair of electrodes made of a conductive material suitable for providing electrolysis,
    b) conductors for conducting current to the electrodes,
    c) an insert unit having a first side and a second side opposite each other, wherein the first side faces out of the water reservoir when the insert unit is placed in position in the water reservoir in use for water disinfection and the second side faces into the volume of the water reservoir when placed in position in the water reservoir in use for water disinfection,
  wherein
    (i) the pair of electrodes is arranged and fixed in the insert unit and protrude from the second side,
    (ii) the conductors are arranged and fixed in the insert unit and protrude from the first side, and
    (iii) the insert unit is adapted for being arranged in an opening in the water reservoir and for a water tight sealing of the water reservoir when in use for water disinfection.

2. The washing system of claim 1 wherein the pair of electrodes is a pair of parallel and symmetrically arranged electrode plates made of a conductive material and having a suitable distance for providing electrolysis, wherein the pair of electrode plates is arranged and fixed in the insert unit and protrudes from the second side.

3. The washing system of claim 2, wherein the pair of parallel and symmetrically arranged electrode plates is perforated and is separated by a distance selected from 1-5 mm.

4. The washing system of claim 1, wherein the electrolysis body comprises a filter unit and wherein the pair of electrodes is at least partially surrounded by the filter unit.

5. The washing system of claim 4, wherein the insert unit and the filter unit are integrated into one unit.

6. The washing system of claim 4, wherein the insert unit and the filter unit are made of a material that does not degrade in the presence of an oxidizing disinfectant and is not electrically conductive.

7. The washing system of claim 6, wherein the oxidizing disinfectant comprises chlorine.

8. The washing system of claim 4, wherein both the insert unit and the filter unit are circular.

9. The washing system of claim 1, wherein the internal volume of the water reservoir is from 1 to 10 liters.

10. The washing system of claim 9, wherein the internal volume of the water reservoir is about 4 liters.

11. The washing system of claim 1, wherein the water reservoir is a grey water tank, having an internal volume of at least 50 litres.

12. The washing system of claim 11, wherein the internal volume is from 50 litres to 10 $m^3$.

13. The washing system of claim 1, wherein the water reservoir has at least two electrolysis bodies.

14. The washing system of claim 1, wherein the insert unit of the electrolysis body is adapted for being arranged in an opening in the water reservoir and for a water tight sealing of the water reservoir when in use for water disinfection, by at least one of thread, glue, bracket or snapping.

* * * * *